United States Patent [19]

Kojima et al.

[11] Patent Number: 4,615,970
[45] Date of Patent: Oct. 7, 1986

[54] SILVER HALIDE PHOTOGRAPHIC MATERIAL

[75] Inventors: Tetsuro Kojima; Koki Nakamura; Takashi Toyoda, all of Kanagawa, Japan

[73] Assignee: Fuji Photo Film Co., Ltd., Kanagawa, Japan

[21] Appl. No.: 678,906

[22] Filed: Dec. 6, 1984

[30] Foreign Application Priority Data

Dec. 7, 1983 [JP] Japan ................................. 58-231088

[51] Int. Cl.⁴ .................................................. G03C 1/34
[52] U.S. Cl. ................................. 430/446; 430/448; 430/614; 430/615; 430/602; 430/372; 430/637
[58] Field of Search ............... 430/614, 615, 446, 448, 430/602, 372, 637

[56] References Cited

U.S. PATENT DOCUMENTS 3,915,710 10/1975 Habu et al. ........................... 430/608
4,378,424 3/1983 Altland et al. ....................... 430/352

Primary Examiner—Won H. Louie
Attorney, Agent, or Firm—Sughrue, Mion, Zinn, Macpeak & Seas

[57] ABSTRACT

A silver halide photographic material containing at least one of compounds represented by formula (I) and salts thereof in at least one hydrophilic colloidal layer of the silver halide photographic material gives photographic images having stable and excellent quality without being accompanied by the increased formation of fog and increased changes of sensitivity and gradation upon high temperature processing:

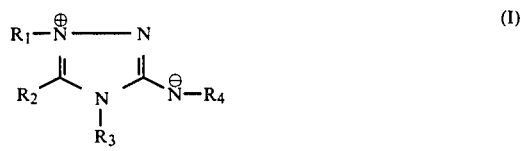

wherein $R_1$, $R_2$, $R_3$ and $R_4$ each represents a substituted or unsubstituted alkyl group, a substituted or unsubstituted alkenyl group, a substituted or unsubstituted cycloalkyl group, a substituted or unsubstituted aryl group, or a substituted or unsubstituted heterocyclic ring group; or one or both of said $R_1$ and $R_2$ and said $R_3$ and $R_4$ combine with each other to form a ring.

34 Claims, No Drawings

SILVER HALIDE PHOTOGRAPHIC MATERIAL

FIELD OF THE INVENTION

This invention relates to a silver halide photographic material and, more particularly, to a silver halide photographic material which can prevent the formation of fog occurring upon high temperature quick processing, effectively control the development speed, and provide a high-quality image.

By the term "effectively control the development speed" is meant that the reliance of a photographic material upon the conditions of the development process is reduced. Practically speaking, one of the meanings is to reduce the difference of a sensitivity obtained at various temperatures of high temperature processing. In other words, it means to reduce the reliance of sensitivity on the temperature of the development process. Another meaning is to reduce as low as possible the influence of highly concentrated halogen ions (in particular, bromide ion) accumulated in a developer during development on the photographic sensitivity. That is, it means to reduce the reliance of sensitivity on halogen ions.

BACKGROUND OF THE INVENTION

Recently, for reducing the processing time for silver halide photographic materials, a process of increasing the development speed by high temperature processing has been employed. "High temperature processing" generally means processing at a temperature higher than 30° C., and the various problems of such a process are well known. In one of the problems, the increase of the development speed causes the increase of the formation of fog, the increase of the change in sensitivity and gradation, and the reduction of graininess and sharpness of images. In another one of the problems, the sensitivity and gradation largely change by the highly concentrated halogen ions (in particular, bromide ions) released and accumulated in a developer during development process, whereby a stable photographic property can not be obtained.

Various methods for overcoming these difficulties are known, but they are insufficient for eliminating these problems. For example, it is known to incorporate in a photographic material nitron as described in Japanese Patent Publication No. 28691/77 (corresponding to U.S. Pat. No. 3,915,710 and German Patent (OLS) No. 2,431,092) or an antifoggant such as 1-phenyl-5-mercaptotetrazole, 5-nitrobenzotriazole, etc. However, nitron may have an antifogging action and a development restraining action but is very insufficient in the point of improving these actions and reducing reliance on the conditions of development. Also, the foregoing antifoggants have a high antifogging action, but the use of such an antifoggant greatly reduces sensitivity and does not improve the halogen reliance in developers.

Thus, silver halide photographic materials which can sufficiently endure severe development conditions required at present have not yet been obtained.

SUMMARY OF THE INVENTION

The first object of this invention is, therefore, to provide a silver halide photographic material which can be processed by high temperature quick processing required at present without being accompanied by the formation of fog, and the extremely increased change in sensitivity and gradation.

The second object of this invention is to provide a silver halide photographic material which shows less change in sensitivity and gradation by the deviation of temperature in high temperature processing.

The third object of this invention is to provide a silver halide photographic material which shows less change in sensitivity and gradation by halogen ions (in particular, bromide ions) accumulated in developer with the increase of the number of processed photographic materials.

The fourth object of this invention is to provide a silver halide photographic material which always gives excellent images by high temperature quick processing.

As the result of various investigations, the inventors have discovered that the above-described objects of this invention can be attained by incorporating at least one of a compound represented by following formula (I) and a salt of the compound to a hydrophilic colloid layer of a silver halide photographic material.

That is, the present invention provides a silver halide photographic material comprising a support having thereon at least one silver halide emulsion layer, and at least one of said silver halide emulsion layer and other hydrophilic colloid layer containing at least one of a compound represented by general formula (I) and a salt formed from said compound and an acid:

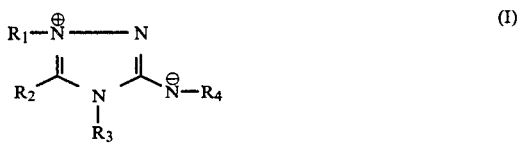

wherein $R_1$, $R_2$, $R_3$ and $R_4$ each represents a substituted or unsubstituted alkyl group, a substituted or unsubstituted alkenyl group, a substituted or unsubstituted cycloalkyl group, a substituted or unsubstituted aryl group, or a substituted or unsubstituted heterocyclic ring group; said $R_1$ and $R_2$ and said $R_3$ and $R_4$ may combine with each other to form a ring.

DESCRIPTION OF THE PREFERRED EMBODIMENT

The compound shown by formula (I) above is explained in more detail. $R_1$, $R_2$, $R_3$ and $R_4$ in general formula (I) represent a substituted or unsubstituted alkyl group having, preferably, from 1 to 30 carbon atoms, such as a methyl group, an ethyl group, an n-propyl group, a t-butyl group, an isobutyl group, an n-pentyl group, an n-undecyl group, an n-heptadecyl group, a methoxymethyl group, a methoxyethyl group, a phenetyl group, etc.; a substituted or unsubstituted alkenyl group having, preferably, from 3 to 30 carbon atoms, such as an allyl group, etc.; a substituted or unsubstituted cycloalkyl group having, preferably, from 3 to 30 carbon atoms, such as a cyclohexyl group, etc.; a substituted or unsubstituted aryl group having preferably, from 6 to 30 carbon atoms, such as a phenyl group, a naphthyl group, a 4-methyl phenyl group, a 4-carboxyphenyl group, a 3,4-dichlorophenyl group, a 4-methanesulfonylphenyl group, a 4-chlorophenyl group, a 4-ethoxycarbonylphenyl group, etc.; or a substituted or unsubstituted heterocyclic ring group (containing at least one hetero atom such as N, O and S atoms) having, preferably, from 1 to 30 carbon atoms, such as a 2-pyridyl group, a 4-pyridyl group, a 2-thienyl group, a 3-furyl group, a 2-quinolyl group, etc.

Examples of substituents of the substituted alkyl, alkenyl, cycloalkyl, aryl and heterocyclic ring group include a halogen atom, an alkoxy group having, preferably, from 1 to 6 carbon atoms, an aryloxy group having, preferably, from 6 to 12 carbon atoms, an amino group, an alkyl amino group having, preferably, from 1 to 6 carbon atoms, an aryl amino group having, preferably, from 6 to 12 carbon atoms, a hydroxy group, a cyano group, a nitro group, an acyl amino group having, preferably, from 2 to 6 carbon atoms, a carbamoyl group having, preferably, from 1 to 6 carbon atoms, a sulfonyl group having, preferably, from 1 to 6 carbon atoms, a sulfamoyl group having, preferably, from 1 to 6 carbon atoms, a sulfonamide group having, preferably, from 0 to 6 carbon atoms, an acyloxy group having, preferably, from 2 to 6 carbon atoms, an alkoxycarbonyl group having, preferably, from 2 to 6 carbon atoms, a carboxyl group, an acyl group having, preferably, from 2 to 6 carbon atoms and a sulfonic acid group. Among these examples preferred substituents are, for example, a halogen atom, an alkoxy group, a hydroxy group, sulfonamide group, an alkoxy carbonyl group and a carboxyl group.

The compound of general formula (I) may form a salt with an acid such as acetic acid, nitric acid, salicylic acid, hydrochloric acid, hydriodic acid, hydrobromic acid, etc.

One or both of said $R_1$ and $R_2$ and said $R_3$ and $R_4$ may form 5 or 6 membered hydrocarbon rings.

In general formula (I), $R_1$, $R_3$ and $R_4$ represent more preferably a substituted or unsubstituted aryl group having from 6 to 20 carbon atoms, and $R_2$ represents more preferably a substituted or unsubstituted alkyl group having from 1 to 10 carbon atoms or a substituted or unsubstituted aryl froup having from 6 to 20 carbon atoms.

Specific examples of the compound shown by foregoing formula (I) are shown below but the compounds of this invention according to formula (I) are not limited to these compounds.

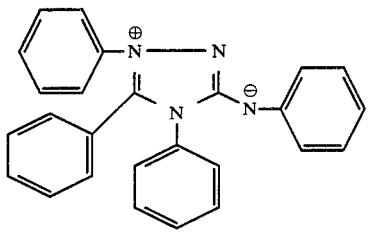

(1)

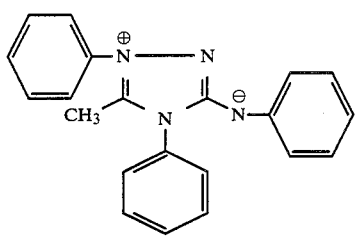

(2)

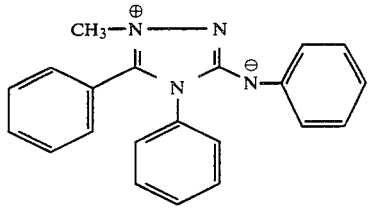

(3)

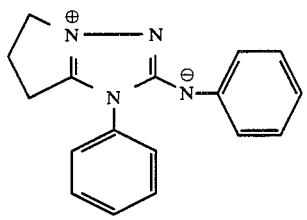

(4)

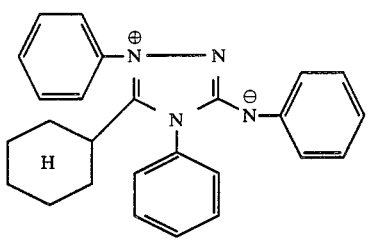

(5)

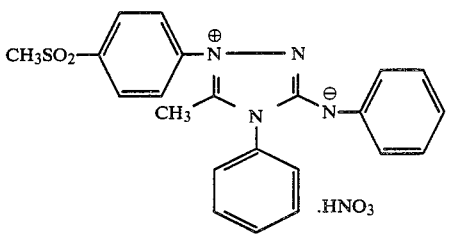

(6)

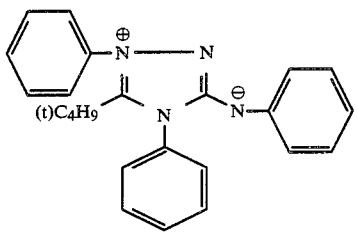

(7)

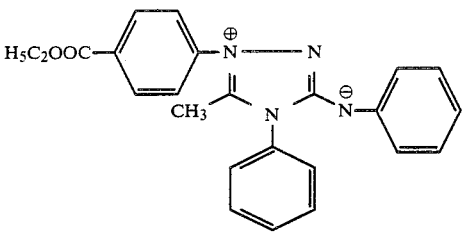

(8)

-continued
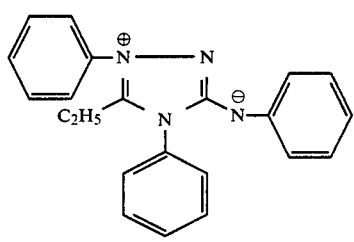 (9)
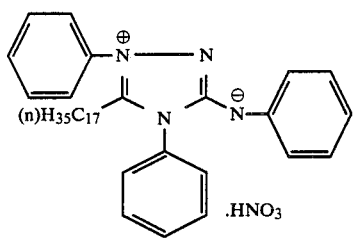 (10)
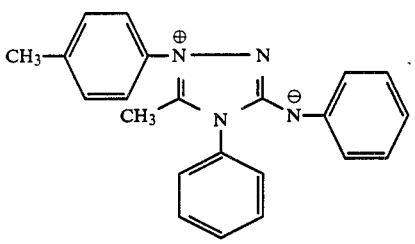 (11)
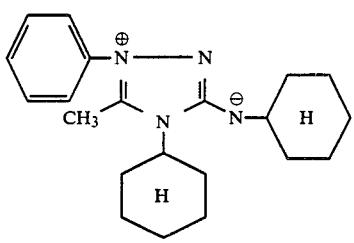 (12)
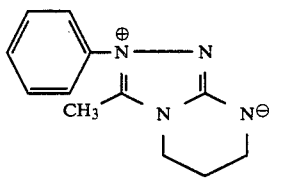 (13)
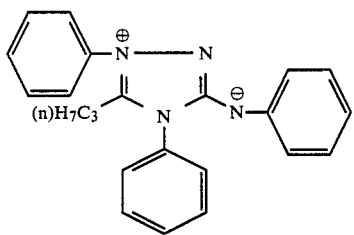 (14)
-continued
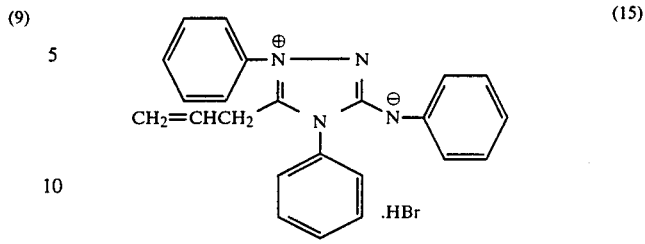 (15)
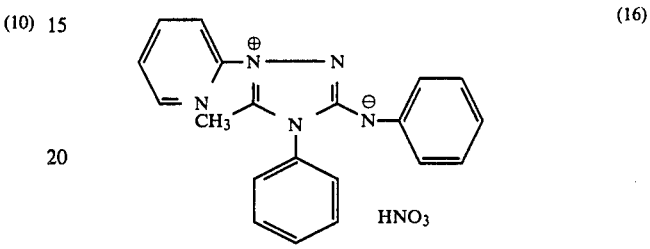 (16)
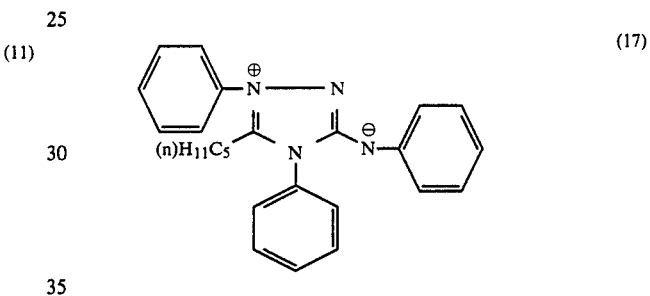 (17)
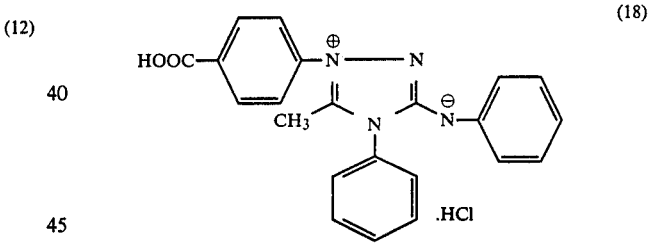 (18)
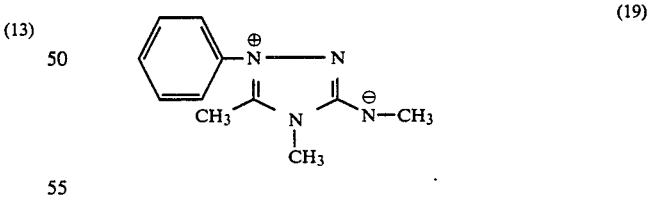 (19)
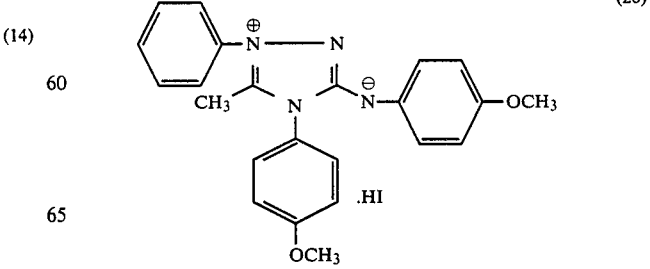 (20)

-continued

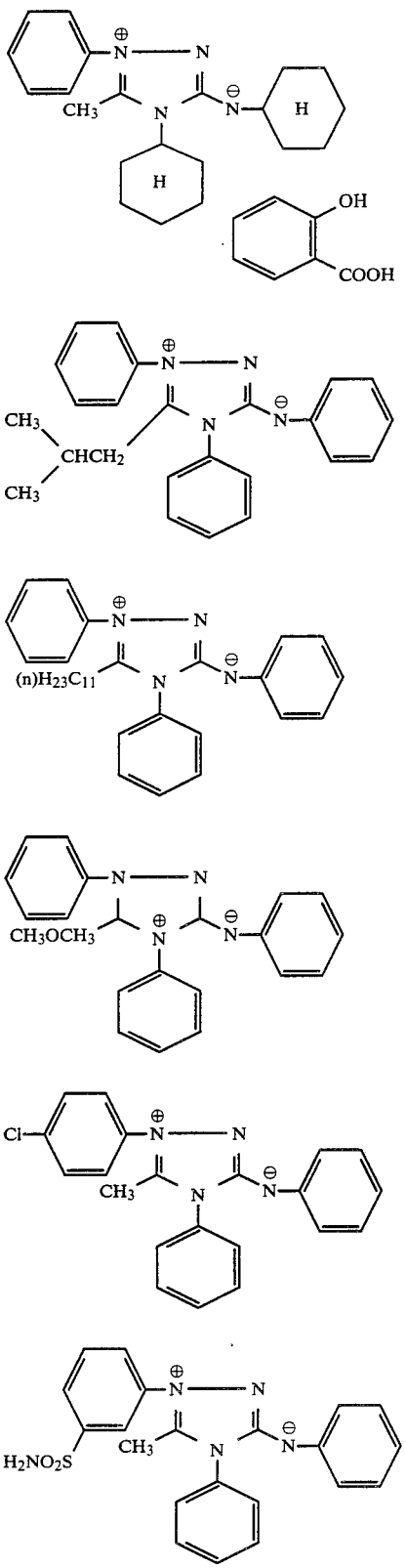

The compounds shown by formula (I) above can be prepared by the methods described, for example, in *Berichte der Deutschen Chemischen Gesellschaft*, Vol. 38, p. 4049 (1905); *Journal of the Chemical Society, Chemical Communications*, 1224 (1971); *Journal of the chemical Society, Perkin Transactions*, I. p. 638 (1974), etc.

Then, specific examples for preparing the compounds of formula (I), which are used in this invention, are illustrated below.

SYNTHESIS EXAMPLE 1

(Synthesis of Compound (1))

To 300 ml of benzene was added 10 g of phenylhydrazine and the mixture was stirred under ice-cooling. To the solution thus formed was added dropwise 17 g of diphenylcarbodiimide and the mixture was stirred for 5 hours as it was to precipitate crystals, which were recovered by suction filtration to provide 16 g of 1,2-diphenyl-3-anilinoguanidine. Then, 5.8 g of the compound thus obtained and 3.4 g of benzoyl chloride were heat refluxed in 100 ml of toluene for 6 hours; after the reaction was over, toluene was distilled off under reduced pressure, and the oily material thus obtained was dissolved in 80 ml of ethanol. After adding 10 ml of aqueous ammonia to the solution, water was gradually added to the mixture, whereby Compound (1) was obtained as light yellow crystals. The yield for the product was 62.1% and the melting point was 226° to 227.5° C.

SYNTHESIS EXAMPLE 2

(Synthesis of Compound (2))

To 9.1 g of 1,2-diphenyl-3-anilinoguanidine prepared as in Synthesis Example 1 was added 100 ml of toluene and then, 4.8 g of acetyl chloride was added to the mixture. After stirring the resultant mixture for 30 minutes at room temperature, the mixture was heat refluxed for 8 hours. After the reaction was over, toluene was distilled off under reduced pressure and the residue thus formed was dissolved in 50 ml of ethanol. 10 ml of aqueous ammonia was added to the solution, and then 40 ml of water was added thereto to precipitate colorless crystals, which were collected by filtration and recrystallized from a mixture of chloroform and hexane to provide 5.8 g of the desired compound. The yield was 59.2% and the melting point was 246° to 247° C.

SYNTHESIS EXAMPLE 3

(Synthesis of Compound (6))

In 140 ml of tetrahydrofuran were dissolved 4.0 g of 4-methanesulfonylphenylhydrazide and 4.6 g of 1,3-diphenylcarbodiimide and after stirring the solution for 2 hours under ice cooling, tetrahydrofuran was distilled off under reduced pressure. To the oily material thus formed were added 50 ml of benzene and 50 ml of n-hexane to precipitate crystals, which were collected by filtration to provide 7.0 g of 1,2-diphenyl-3-(4-methanesulfonylphenylamino)guanidine.

Then, 30 ml of toluene was added to 2.0 g of 1,2-diphenyl-3-(4-methanesulfonylphenylamino)guanidine and after further adding thereto 0.7 ml of acetyl chloride, the mixture was heat refluxed for 5 hours. Thereafter, toluene was distilled off under reduced pressure. The solid residue thus formed was dissolved in 30 ml of ethanol and then 10 ml of aqueous ammonia and 50 ml of water were added to the solution to precipitate crystals, which were collected by filtration and dissolved in 30 ml of acetic acid. Then, a solution of 0.85 g of ammonium nitrate dissolved in 30 ml of water was added to the above solution to precipitate crystals, which were collected by filtration and recrystallized from a mixture of ethyl acetate and methanol to provide 1.2 g of the desired compound. The yield was 48.4% and the melting point was 212° to 213° C.

SYNTHESIS EXAMPLE 4

(Synthesis of Compound (7))

To 9.1 g of 1,2-diphenyl-3-anilinoguanidine prepared as in Synthesis Example 1 was added 100 ml of toluene and the mixture was stirred. To the mixture was added 5.8 g of pivalyl chloride at room temperature and the resultant mixture was stirred for 30 minutes. Then, the mixture was heat refluxed for 5 hours. After the reaction was over, toluene was distilled off and the residue thus formed was dissolved in 50 ml of ethanol. Then, 10 ml of aqueous ammonia and 40 ml of water were added to the solution ot precipitate crystals, which were collected by filtration and recrystallized from a mixture of chloroform and n-hexane to provide 65 g of the desired compound. The yield was 58.8% and the melting point was 250° to 255° C.

SYNTHESIS EXAMPLE 5

(Synthesis of Compound (8))

In 70 ml of tetrahydrofuran were dissolved 9.0 g of 4-ethoxycarbonylphenylhydrazine and 9.7 g of 1,3-diphenylcarbodiimide and after stirring the solution for one hour under ice-cooling, tetrahydrofuran was distilled off under reduced pressure. Then, when 70 ml of benzene and 70 ml of n-hexane were added to the residue thus formed, crystals deposited. By collecting the crystals thus deposited by filtration, 15.4 g of 1,2-diphenyl-3-(4-ethoxycarbonylphenylamino)guanidine was obtained.

Then, to 5.5 g of 1,2-diphenyl-3-(4-ethoxycarbonylphenylamino)guanidine were added 50 ml of toluene and 2.1 ml of acetyl chloride and after heat refluxing the mixture for 6 hours, toluene was distilled off under reduced pressure. The residue thus formed was dissolved in 50 ml of ethanol and then 20 ml of aqueous ammonia and 30 ml of water were added to the solution to precipitate crystals, which were collected by filtration and recrystallized from a mixture of ethyl acetate and methanol to provide 3.0 g of the desired compound. The yield was 51.2% and the melting point was 217° to 218° C.

SYNTHESIS EXAMPLE 6

(Synthesis of Compound (11))

In 250 ml of tetrahydrofuran were dissolved 8.6 g of 4-methylphenylhydrazine and 15.0 g of 1,3-diphenylcarbodiimide and after stirring the solution for 2 hours under ice-cooling, tetrahydrofuran was distilled off under reduced pressure. When 40 ml of benzene and 80 ml of n-hexane were added to the oily product thus formed, crystals deposited. By collecting the crystals thus deposited by filtration, 5.9 g of 1,2-diphenyl-3-(4-methylphenylamino)guanidine was obtained.

Then, 3.2 g of 1,2-diphenyl-3-(4-methylphenylamino)guanidine were added 30 ml of toluene and 0.9 ml of acetyl chloride and after heat refluxing the mixture for 4 hours, toluene was distilled off under reduced pressure. The solid residue thus formed was dissolved in 50 ml of ethanol and then 15 ml of aqueous ammonia and 30 ml of water were added to the solution to precipitate crystals, which were collected by filtration and recrystallized from a mixture of ethyl acetate and methanol to provide 0.7 g of the desired product. The yield was 20.6% and the melting point was 248° to 252° C.

SYNTHESIS EXAMPLE 7

(Synthesis of Compound (18))

To 1.0 g of Compound 8 prepared as in Synthesis Example 5 were added 30 ml of water and 5 ml of concentrated hydrochloric acid and the mixture was heat refluxed for 3 hours to precipitate crystals, which were collected by filtration and recrystallized from a mixture of ethyl acetate and methanol to provide 0.8 g of the desired product. The yield was 80.0% and the melting point was 285° to 288° C.

The compounds of general formula (I) may be used solely or as a mixture thereof.

The foregoing compounds which are used in this invention may be incorporated in any hydrophilic colloidal layers of silver halide photographic materials, such as silver halide emulsion layers, subbing layers, protective layers, interlayers, filter layers, antihalation layers, etc., and preferably be incorporated in a silver halide layer.

For incorporating the foregoing compound in these photographic layers, the compound may be added to the coating liquid for forming the photographic layer as it is or as a solution in a solvent giving no bad influences on the photographic material, such as water, alcohol, etc., in a proper concentration. Also, the compound may be dispersed by emulsification in the aqueous solution for the photographic layer as a solution in a high boiling organic solvent or a low boiling organic solvent. Furthermore, the compound may be added to the coating liquid for the photographic layer as a polymer latex impregnated with the compound by the method described in Japanese Patent Application (OPI) Nos. 39853/76, 59942/76 and 32552/79 (the term "OPI" as used herein refers to a "published unexamined Japanese Patent Application"), U.S. Pat. No. 4,100,363, etc.

The compound may be added to the coating liquid for the photographic layer in any step during the production of the photographic material but it is generally preferred to incorporate the compound directly before coating the coating liquid.

The addition amount of the compound is generally from $10^{-8}$ to $10^{-1}$ mole, preferably from $1\times10^{-5}$ to $10^{-2}$, and more preferably from $5\times10^{-5}$ to $7\times10^{-3}$ mole per mole of silver in the photographic material.

The silver halide for use in this invention includes silver chloride, silver bromide, silver iodide, silver chlorobromide, silver chloroiodide, silver iodobromide, silver chloroiodobromide, etc.

These silver halide grains may be coarse grains, fine grains, or mixed grains thereof, and the silver halide grains are formed by a known method such as a single jet method, a double jet method, and a controlled double jet method.

The silver halide grains for use in this invention may have a regular crystal form such as a cubic form, an octehedron, and a tetradecahedron, or may have an irregular form such as a spherical form and a tabular form, or further may have a composite form of these crystal forms. Moreover, the silver halide may be composed of a mixture of various crystal forms.

Also, the silver halide grains for use in this invention may be tabular grains having an aspect ratio of higher than 5 as described in Japanese Patent Application (OPI) Nos. 127,921/'83, 113,927/'83, etc.

Furthermore, the silver halide grains may have a crystal structure having a uniform property throughout the grains, a layer structure having different property between the internal portion and the external portion of the grain, or of a so-called conversion type as described in British Pat. No. 635,841 and U.S. Pat. No. 3,622,318. Also, the silver halide grains may be of a type forming a latent image mainly on the surface of the grain or of an internal latent image type forming a latent image in the internal portion of the grain. The silver halide photographic emulsion containing these silver halide grains can be prepared by various methods such as an ammonia method, a neutralization method, an acid method, etc., as described in, for example, Mees, *The Theory of Photographic Process*, published by MacMillan Co., Glafkides, *Photographic Chemistry*, published by Fountain Press Co., *Research Disclosure*, Vol. 176 (December, 1978), RD-17643, etc.

The mean diameter of silver halide grains which are used in this invention is preferably from about 0.04 micron to about 4 microns (measured by, for example, a number average method using a projected area method).

During the formation of the silver halide grains, ammonia, potassium thiocyanate, ammonium thiocyanate, thioether compounds (described in, e.g., U.S. Pat. Nos. 3,271,157, 3,574,628, 3,704,130, 4,297,439, 4,276,374, etc.), thion compounds (described in, for example, Japanese Patent Application (OPI) Nos. 144319/78, 82408/78, 77737/80, etc.), amine compounds (described in, for example, Japanese Patent Application (OPI) No. 100717/79), etc., as a silver halide solvent for controlling the growth of the silver halide grains.

Also, during the formation of the silver halide grains or before or after the formation of the silver halide grains, a water-soluble rhodium compound and/or a water-soluble iridium compound may be added to the system.

The silver halide photographic emulsions for use in this invention can be sensitized by an ordinary chemical sensitization method, such as a gold sensitization (as described in U.S. Pat. Nos. 2,540,085, 2,597,876, 2,597,915, 2,399,083, etc.), a sensitization by the ion of a metal belonging to group VIII of the Periodic Table (described in U.S. Pat. Nos. 2,448,060, 2,540,086, 2,566,245, 2,566,263, 2,598,079, etc.), a sulfur sensitization (described in U.S. Pat. Nos. 1,574,944, 2,278,947, 2,440,206, 2,521,926, 3,021,215, 3,038,805, 2,410,689, 3,189,458, 3,415,649, 3,635,717, etc.), a reduction sensitization (described in U.S. Pat. Nos. 2,518,698, 2,419,974, 2,983,610, *Research Disclosure*, Vol. 176 (December, 1978), RD-17643, Chapter III, etc.), a sensitization by a thioether compound (described in U.S. Pat. Nos. 2,521,926, 3,021,215, 3,038,805, 3,046,129, 3,046,132, 3,046,133, 3,046,134, 3,046,135, 3,057,724, 3,062,646, 3,165,552, 3,189,458, 3,192,046, 3,506,443, 3,671,260, 3,574,709, 3,625,697, 3,635,717, 4,198,240, etc.), or a combination of these sensitization methods.

More practically, the chemical sensitizer for use in the foregoing chemical sensitization includes a sulfur sensitizer such as allyl thiocarbamide, thiourea, sodium thiosulfate, thioether, cystine, etc.; a noble metal sensitizer such as potassium chloroaurate, aurous thiosulfate, potassium chloropalladate, etc.; and a reduction sensitizer such as tin chloride, phenylhydrazine, reductone, etc.

Other examples of the sensitizers which can be also used in this invention are polyoxyethylene derivatives (described in British Pat. No. 981,470, Japanese Patent Publication No. 6475/66, British Pat. No. 2,716,062, etc.), polyoxypropylene derivatives, derivatives having a quaternary ammonium group, etc.

To the silver halide photographic emulsions for use in this invention may be added various compounds for preventing the reduction in sensitivity and the formation of fog during the production, storing, and processing of the photographic materials. As these compounds, well-known are nitrobenzimidazole, ammonium chloroplatinate, 4-hydroxy-6-methyl-1,3,3a,7-tetraazaindene, 3-methylbenzothiazole, 1-phenyl-5-mercaptotetrazole, various heterocyclic compounds, mercury-containing compounds, mercapto compounds, metal salts, etc. Other examples of the compounds which can be used for the foregoing purposes in this invention described in K. Mees, *The Theory of the Photographic Process*, 3rd Edition, 1966, from page 344 to page 349 together with the original literature cited therein include the thiazolium salts described in U.S. Pat. Nos. 2,131,038, 2,694,716, etc.; the azaindenes described in U.S. Pat. Nos. 2,886,437, 2,444,605, etc.; the urazols described in U.S. Pat. No. 3,287,135, etc.; the sulfocatechols described in U.S. Pat. No. 3,236,652, etc.; the oximes described in British Pat. No. 623,448, etc.; the mercaptotetrazoles described in U.S. Pat. Nos. 2,403,927, 3,266,897, 3,397,987, etc.; nitron; nitroindazoles; the polyvalent metal salts described in U.S. Pat. No. 2,839,405, etc.; the thiuronium salts described in U.S. Pat. No. 3,220,839, etc.; and the salts of palladium, platinum, and gold described in U.S. Pat. Nos. 2,566,263, 2,597,915, etc.

The silver halide emulsions for use in this invention can be sensitized by using spectral sensitizing dyes. Examples of such sensitizing dyes are described in, for example, U.S. Pat. Nos. 3,703,377, 2,688,545, 3,397,060, 3,615,635, 3,628,964, British Pat. Nos. 1,242,588 and 1,293,862, Japanese Patent Publication Nos. 4936/68, 14030/69 and 10773/68, U.S. Pat. No. 3,416,927, Japanese Patent Publication No. 4930/68, U.S. Pat. Nos. 3,615,613, 3,615,632, 3,617,295, 3,635,721, etc.

Also, if necessary, these sensitizing dyes may be used as a combination thereof.

The silver halide emulsions may be hardened by an ordinary method. Examples of the hardening agent which can be used for the purpose are aldehyde compounds such as formaldehyde, glutaraldehyde, etc.; ketone compounds such as diacetyl, cyclopentanedione, etc.; compounds having a reactive halogen such as bis(2-chloroethylurea), 2-hydroxy-4,6-dichloro-1,3,5-triazine, as well as those as shown in U.S. Pat. Nos. 3,288,775, 2,732,303, British Pat. Nos. 974,723, 1,167,207, etc.; compounds having a reactive olefin such as divinylsulfone, 5-acetyl-1,3-diacryloylhexahydro-1,3,5-triazine as well as those as shown in U.S. Pat. Nos. 3,635,718, 3,232,763, British Pat. No. 994,869, etc.; N-methylol compounds such as N-hydroxymethylphthalimide and those as shown in U.S. Pat. Nos. 2,732,316, 2,586,168, etc.; the isocyanates as shown in U.S. Pat. No. 3,103,437, etc.; the aziridine compounds as shown in U.S. Pat. Nos. 3,017,280, 2,983,611, etc.; the acid derivatives as shown in U.S. Pat. Nos. 2,725,294, 2,725,295, etc.; the carbodiimide series compounds as shown in U.S. Pat. No. 3,100,704, etc.; the epoxy compounds as shown in U.S. Pat. No. 3,091,537, etc.; the isooxazole compounds as shown in U.S. Pat. Nos. 3,321,313, 3,543,292, etc.; halogenocarboxyaldehydes such as mucochloric acid, etc.; dioxane derivatives such as dihydroxydioxane, dichlorodioxane, etc.; and inorganic hardening agents such as chromium alum, zirconium sulfate, etc.

Also, in place of the foregoing compounds, precursors of them, such as, for example, alkali metal bisulfite-aldehyde addition products, methylol derivatives of hydantoin, primary aliphatic nitroalcohols, etc., may be used as hardening agents.

The silver halide photographic emulsions for use in this invention may contain surface active agents solely or as a mixture of them. These surface active agents are mainly used as a coating aid but are used for other purposes such as for improving the emulsifying dispersion, for improving sensitization characteristics, for antistatic prevention, for preventing adhesion of photographic materials, etc. These surface active agents include natural surface active agents such as saponin, etc.; nonionic surface active agents such as alkylene oxide series surface active agents, glycerol series surface active agents, glycidol series surface active agents, etc.; cationic surface active agents such as higher alkylamines, quaternary ammonium salts, pyridine and other heterocyclic rings, phosphonium salts, sulfonium salts, etc.; anionic surface active agents having an acid group such as a carboxylic acid group, a sulfonic acid group, a phosphoric acid group, a sulfuric acid ester group, a phosphoric acid ester group, etc.; and amphoteric surface active agents such as amino acids, aminosulfonic acids, sulfuric acid esters or phosphoric acid esters of aminoalcohol, etc.

The polyalkylene oxide compounds which can be used in this invention include the condensation products of polyalkylene oxide composed of an alkylene oxide having 2 to 4 carbon atoms, such as ethylene oxide, propylene-1,2-oxide, butylene-1,2-oxide, etc., preferably composed of at least 10 units of ethylene oxide and a compound having at least one active hydrogen, such as water, an aliphatic alcohol, an aromatic alcohol, a fatty acid, an organic amine, a hexytol derivatives, etc.; and a block copolymer of two or more kinds of polyalkylene oxides.

Specific examples of such polyalkylene oxide compounds are polyalkylene glycols, polyalkylene glycol alkyl ethers, polyalkylene glycol aryl ethers, polyalkylene glycol alkylaryl ethers, polyalkylene glycol esters, polyalkylene glycol fatty acid amines, polyalkylene glycol amines, polyalkylene glycol block copolymers, polyalkylene glycol graft polymers, etc. It is necessary that the molecular weight of the polyalkylene oxide compound for use in this invention is higher than 600.

Among these polyalkylene oxide compounds, particularly preferred compounds are those shown by following formulae (II), (III), and (IV):

$$R-A(CH_2CH_2O)_{n_1}-H \quad (II)$$

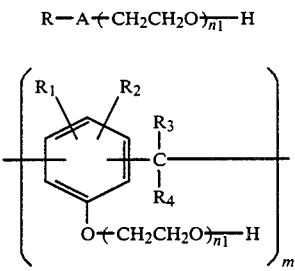 (III)

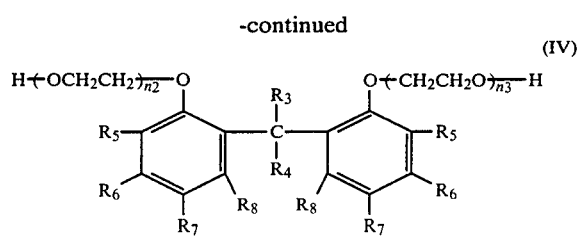 (IV)

wherein R represents a substituted or unsubstituted alkyl group having 1 to 30 carbon atoms, alkenyl group having from 3 to 30 carbon atoms, or aryl group having from 6 to 30 carbon atoms; A represents —O— group, —S— group, —COO— group, $-N-R_{11}$ group, $-CO-N-R_{11}$ group or $-SO_2N-R_{11}$ group
   |                    |                           | wherein $R_{11}$ represents a hydrogen atom or a substituted or unsubstituted alkyl group having preferably from 1 to 30 carbon atoms; $R_1$, $R_2$, $R_6$ and $R_8$ each represents a hydrogen atom, a substituted or unsubstituted alkyl group, aryl group, or alkoxy group, a halogen atom, an acyl group, an amido group, a sulfoamide group, a carbamoyl group or a sulfamoyl group and $R_5$ and $R_7$ each represents a substituted or unsubstituted alkyl group, aryl group, or alkoxy group, a halogen atom, an acyl group, an amido group, a sulfonamido group, a carbamoyl group or a sulfamoyl group; said $R_5$ and $R_6$, said $R_6$ and $R_7$ or said $R_7$ and $R_8$ may combine with each other to form a substituted or unsubstituted ring such as a 5 or 6 membered hydrocarbon ring; $R_3$ and $R_4$ each represents a hydrogen atom, a substituted or unsubstituted alkyl group, aryl group, or α-furyl group; said $R_3$ and $R_4$ may combine with each other to form a ring such as a 5 or 6 membered hydrocarbon ring; $n_1$, $n_2$ and $n_3$ each represents a mean polymerization degree of the ethylene oxide, which is a number of 2 to 50; and m represents a mean polymerization degree, which is a number of 2 to 50. In formula (IV), $R_5$ and $R_6$ may be symmetric or asymmetric to $R_7$ and $R_8$ in the benzene ring.

Examples of substituents of substituted groups represented by R, $R_{11}$ and $R_{1-8}$ and rings comprising of $R_{3-8}$ are the same as disclosed in the description of formula (I).

Specific examples of the polyalkylene oxide compounds shown by formulae (II), (III) and (IV) are shown below.

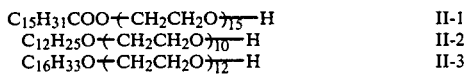

| | |
|---|---|
| $C_{15}H_{31}COO(CH_2CH_2O)_{15}-H$ | II-1 |
| $C_{12}H_{25}O(CH_2CH_2O)_{10}-H$ | II-2 |
| $C_{16}H_{33}O(CH_2CH_2O)_{12}-H$ | II-3 |

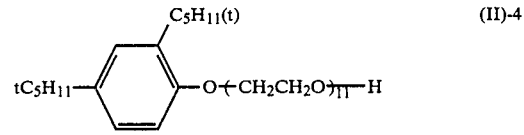 (II)-4

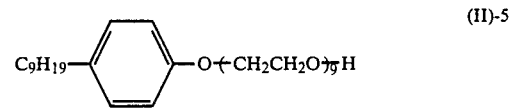 (II)-5

-continued (III)-1 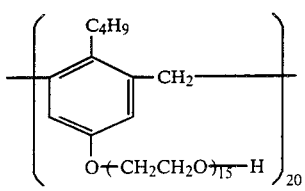

(III)-2 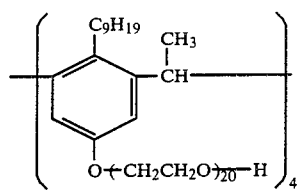

(III)-3 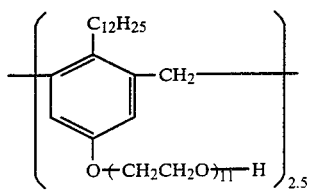

(IV)-1 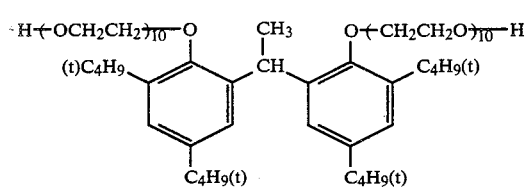

(IV)-2 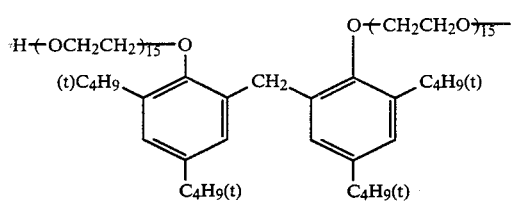

(IV)-3 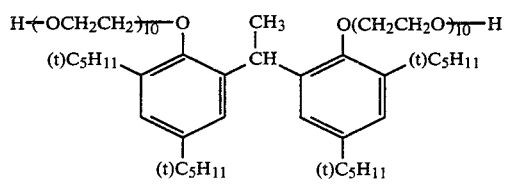

(IV)-4 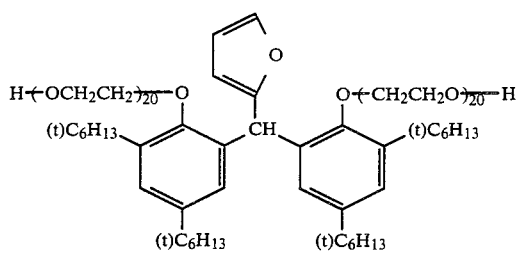

-continued (IV)-5 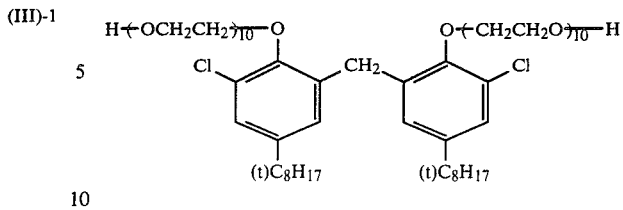

(IV)-6 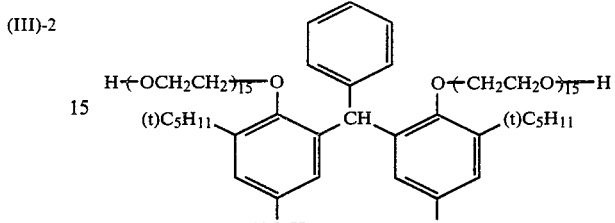

(IV)-7 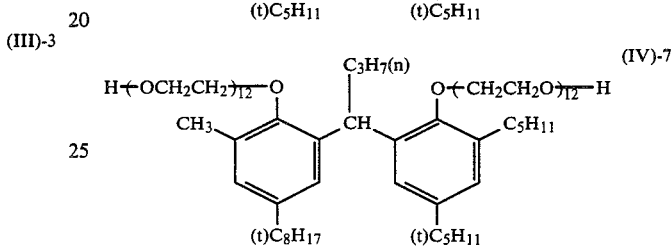

By using the aforesaid polyalkylene oxide compound described above together with compound of the invention, the reliance of the silver halide photographic materials upon the conditions of development process can be more reduced.

The polyalkylene oxide may be incorporated in any layer of a silver halide photographic material, preferably in a hydrophilic layer, and preferably incorporated in the same layer as the layer wherein the compound represented by formula (I) and/or salt thereof is incorporated. The amount of the polyalkylene oxide in a photographic material is usually from 5 to 500 mg/m$^2$, preferably from 20 to 200 mg/m$^2$. The weight ratio of the amount of the polyalkylene oxide to that of the compound represented by formula (I) and/or salt thereof is preferably from 1/10 to 100, and more preferably from 1 to 10.

This invention can be applied to color photographic materials. In this case, for the color reproduction, a subtractive color photographic process is usually used, and silver halide emulsions selectively sensitive to blue, green and red and yellow, magenta, and cyan color formers which are in a complementary color relationship with the aforesaid colors are used. For forming a yellow color image couplers, for example, acylacetanilide series couplers, dibenzoylmethane series couplers, etc., are used for forming a magenta color image, pyrazolone, pyrazolobenzimidazole, cyanoacetophenone, and indazolone series couplers are mainly used. For forming a cyan color image, phenol series couplers such as phenols and naphthols are mainly used.

Specific examples of the magenta coloring couplers are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No.

6031/65, Japanese Patent Application (OPI) Nos. 20826/76, 58922/77, 129538/74, 74027/74, 159336/75, 42121/77, 74028/74, 60233/75, 26541/76, 66122/78, etc.

Specific examples of the yellow coloring couplers are described in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77, 115219/77, etc.

Specific examples of the cyan coloring couplers are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830, 2,454,329, Japanese Patent Application (OPI) Nos. 59838/73, 26034/76, 5055/73, 146828/76, 69624/77, 90932/77, etc.

The color photographic materials of this invention can further contain colored couplers described in, for example, U.S. Pat. Nos. 3,476,560, 2,521,908 and 3,034,892, Japanese Patent Publication Nos. 2016/69, 22335/63, 11304/67, 32461/69, Japanese Patent Application (OPI) Nos. 26034/76 and 42121/77, West German Patent Application (OLS) No. 2,418,959, etc.

The color photographic materials of this invention can also contain development inhibitor releasing (DIR) couplers described in, for example, U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, Japanese Patent Application (OPI) Nos. 69624/77 and 122335/74, Japanese Patent Publication No. 16141/76, etc.

Other than the DIR couplers, the photographic material of this invention may contain compounds which release a development inhibitor with the progress of development. Specific examples of such compounds are described in, for example, U.S. Pat. Nos. 3,297,445 and 3,379,529, West German Patent Application (OLS) No. 2,417,914, Japanese Patent Application (OPI) Nos. 15271/77, 9116/78, etc.

These compounds may be incorporated in silver halide emulsions or aqueous solution of hydrophilic colloid by conventional methods. For example, the couplers can be dispersed by a method of dispersing the coupler as a mixture with a high boiling organic solvent such as dibutyl phthalate, tricresyl phosphate, wax, higher fatty acid or an ester thereof, etc., as described in, for example, U.S. Pat. Nos. 2,304,939, 2,322,027, etc.; by dispersing after mixing the coupler with a low boiling organic solvent or a water-soluble organic solvent; by dispersing after further mixing therewith a high boiling organic solvent as described in, for example, U.S. Pat. Nos. 2,801,170, 2,801,171, 2,949,360, etc.; by dispersing the coupler, when the coupler itself has a sufficiently low melting point (e.g., lower than 75° C.), alone or together with other coupler such as a colored coupler or an uncolored coupler as described in, for example, German Pat. No. 1,143,707, etc.

For dispersing the couplers, ordinary auxiliary dispersing agents may be used and as such auxiliary dispersing agents, there are anionic surface active agents (e.g., sodium alkylbenzenesulfonate, sodium dioctylsulfosuccinate, sodium dodecylsulfate, sodium alkylnaphthalenesulfonate, Fischer-type couplers, etc.), amphoteric surface active agents (e.g., N-tetradecyl-N,N-dipolyethylene a-betaine, etc.), and nonionic surface active agents (e.g., sorbitan monolaurate, etc.).

The silver halide photographic emulsions for use in this invention may contain acylated gelatin such as phthalated gelatin and malonated gelatin; cellulose compounds such as hydroxyethyl cellulose, carboxymethyl cellulose, etc.; soluble starch such as dextrin, etc.; hydrophilic polymers such as polyvinyl alcohol, polyvinyl pyrrolidone, polyacrylamide, polystyrene sulfonic acid, etc., as a protective colloid in place of or in addition to gelatin.

Furthermore, the silver halide photographic emulsions may contain the polymer latexes composed of the homopolymer of copolymer of alkyl acrylate, alkyl methacrylate, acrylic acid, glycidyl acrylate, etc., for improving the dimensional stability of the photographic materials and for improving the properties of the films as disclosed in U.S. Pat. Nos. 3,411,911, 3,411,912, 3,142,568, 3,325,286 and 3,547,650 and Japanese Patent Publication No. 5331/60.

Moreover, the silver halide photographic emulsion of this invention may contain a developing agent such as hydroquinones, catechols, aminophenols; 3-pyrazolidones; ascorbic acid or the derivatives thereof; reductones, phenylenediamines; and a combination of these developing agents. The developing agent can be incorporated in a silver halide emulsion layer and/or other photographic layers (e.g., a protective layer, interlayers, a filter layer, an antihalation layer, a backing layer, etc.), preferably in a silver halide emulsion layer.

The developing agent can be added to the coating composition for the desired photographic layer as a solution in a proper solvent or as a dispersion of it as described in U.S. Pat. No. 2,592,368, French Patent No. 1,505,778, etc.

Examples of the development accelerators which can be used in this invention are described in, for example, U.S. Pat. Nos. 3,288,612, 3,333,959, 3,345,175, 3,708,303, British Pat. No. 1,098,748, and West German Pat. Nos. b 1,141,531, 1,183,784, etc.

The silver halide photographic emulsions for use in this invention may further contain antistatic agents, plasticizers, optical whitening agents, air fogging preventing agents, toning agents, etc. Specific materials of them are described in *Research Disclosure*, Vol. 176 (December, 1978), RD-17643.

The compounds represented by formula (I) can be widely used for various photographic materials, for example, black-and-white photographic materials such as radiographic films (e.g., direct X-ray films, industrial X-ray films), general black-and-white photographic films, lithographic films, scanner films, black-and-white photographic papers, etc.; color photographic materials such as color negative films, color reversal films, color photographic papers, etc., as well as color photographic materials by a silver salt process or a color diffusion transfer photographic process; and color photographic materials by a silver dye bleaching process.

The exposure for obtaining a photographic image using the photographic materials of this invention may be performed by using an ordinary method. That is, various light sources such as natural light (sunlight), a tungsten lamp, a fluorescent lamp, a mercury lamp, a xenon arc lamp, a carbon arc lamp, a xenon flash lamp, flying spot cathode ray tube, light emitting diode, laser light (e.g., gas laser, YAG laser, dye laser, semiconductor laser, etc.) including infrared rays. Also, the light emitted from a phosphor excited by electron beam, X-rays, γ-rays, α-rays, etc., may be employed as the light source.

The exposure time is usually from 1/1,000 sec to 1 sec as for camera use but may be shorter than 1/1,000 sec, for examle, an exposure of $1/10^4$ to $1/10^6$ sec as the case of using a xenon flash lamp or a cathode ray tube, or may be longer than 1 sec. If necessary, the spectral composition of light used for the exposure can be controlled using color filter or filters.

There is no particular restriction about the development process of the silver halide photographic materials of this invention, and, for example, the known processes and known processing liquids described in Research Disclosure, Vol. 176, pages 28–30 can be employed in this invention. The photographic process may be a photographic process for forming silver images (black-and-white photographic process) or a photographic process for forming dye images (color photographic process) according to the purposes. The processing temperature is usually selected from the range of 18° C. to 50° C. but may be lower than 18° C. or over 50° C.

For the silver halide photographic materials, a high-temperature quick processing process, for example, at a processing temperature of 30° C. to 50° C. for a processing time of 20 sec to 240 sec (preferably 20 to 150 seconds, for black and white photographic process and 120 to 240 seconds for color photographic process) is preferably applied. That is, the silver halide photographic materials of this invention causes less formation of fog and less deviation of photographic properties when the photographic materials are processed by the high-temperature quick processing process.

A developer which is used for a black-and-white photographic process can contain known developing agents such as dihydroxybenzenes (e.g., hydroquinone), 3-pyrazolidones (e.g., 1-phenyl-3-pyrazolidone, etc.), aminophenols (e.g., N-methyl-p-aminophenol, etc.), etc. They can be used solely or as a combination thereof. The developers may further contain preservatives, alkali agents, pH buffers, antifoggants, etc., and further, if necessary, dissolution aids, toning agents, development accelerators, surface active agents, defoaming agents, water softeners, hardening agents, tackifiers, etc.

To the silver halide photographic emulsions in this invention can be applied a so-called "lithographic type" development process. By the term "lithographic type" development process is meant a development process for infectiously performing the development step usually using dihydroxybenzene as a developing agent under a low sulfite ion concentration for the photographic reproduction of line images or the photographic reproduction of a halftone image by dot. Details are described in Mason, Photographic Processing Chemistry, pages 163–165 (1966).

A color image can be obtained by an ordinary process. For example, there are a nega-posi process (described in, for example, Journal of the Society of Motion Picture and Television Engineers, Vol. 61, 667 to 701 (1953)), a color reversal process wherein the photographic material is developed in a developer containing a black-and-white developing agent to form a negative silver image and then by performing at least one overall light exposure or other suitable fogging treatment and then performing a color development, a positive dye image is obtained; and a silver dye bleaching process wherein after imagewise exposing a silver halide emulsion layer containing a dye, the emulsion layer is developed to form a silver image and the dye in the emulsion layer is bleached with the silver image as the bleaching catalyst.

A color developer is generally composed of an alkaline aqueous solution containing a color developing agent. For the color developer, known primary aromatic amine developing agent such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc.) can be used.

Other color developing agents which can be used for developing the color photographic materials of this invention are described in L.F.A. Mason, Photographic Processing Chemistry, pages 226–229, published by Focal Press, 1966, U.S. Pat. Nos. 2,193,015 and 2,592,364, Japanese Patent Application (OPI) No. 64933/73, etc.

After color development, the photographic material is usually bleached. The bleach process may be performed simultaneously with fix process or may be performed separately therefrom. As the bleaching agent, there are compounds of multivalent metals such as iron (III), cobalt (IV), chromium (VI), copper (II), etc., peracids, quinones, nitroso compounds, etc.

Then, the following examples are intended to illustrate this invention in more detail but not to limit in any way.

EXAMPLE 1

A silver halide emulsion was prepared as follows. An aqueous solution of silver nitrate and an aqueous solution of an alkali halide were added to an aqueous gelatin solution by an ordinary ammonia method to form silver iodobromide grains (Agi: 2 mole%) having a mean grain size of $1.0\mu$ and then applying thereto a gold and sulfur sensitization using chloroauric acid and sodium thiosulfate and then adding 4-hydroxy-6-methyl-1,3,3a,7-tetraazaindene to the emulsion as a stabilizer, a photosensitive silver iodobromide emulsion was prepared.

After adding each of the compounds illustrated in Table 1 to each of the silver halide emulsions thus prepared, each of the resultant emulsions was coated on a film support to provide Samples 1 to 8. Each of the samples was stepwise exposed through an optical wedge using a sensitometer and after processing the sample by an Automatic Processor RU (made by Fuji PHoto Film Co., Ltd.) using following Developer A and Fix Solution A for 90 seconds at a development temperature of 31° C., 35° C. and 37° C., the photographic properties were measured and the results thus obtained are shown in Table 1 below.

| Developer A | |
|---|---|
| Ethylenediaminetetraacetate | 1.2 g |
| Sodium Sulfite (anhydrous) | 50.0 g |
| Potassium Hydroxide | 20.0 g |
| Hydroquinone | 25.0 g |
| 1-Phenyl-3-pyrazolidone | 1.5 g |
| Boric Acid | 10.0 g |
| Triethylene Glycol | 25.0 g |
| Glutaraldehyde | 5.0 g |
| Potassium Bromide | 6.0 g |
| Glacial Acetic Acid | 3.0 g |
| Sodium Hydrogensulfite (anhydrous) | 4.5 g |

-continued

| Developer A | |
|---|---|
| 5-Nitroindazole | 0.15 g |
| 5-Methylbenzotriazole | 0.03 g |
| Water to make | 1 liter |

The pH of the composition was adjusted to about 10.30 at 25° C.

| Fix Solution A | |
|---|---|
| Ammonium Thiosulfate | 200.0 g |
| Sodium Sulfite (anhydrous) | 20.0 g |
| Boric Acid | 8.0 g |
| Ethylenediaminetetraacetic Acid | 0.1 g |
| Aluminum Sulfate | 15.0 g |
| Sulfuric Acid | 2.0 g |
| Glacial Acetic Acid | 22.0 g |
| Water to make | 1 liter |

The pH of the composition was adjusted to about 4.10 at 25° C.

In addition, the sensitivity shown in Table 1 is reciprocal of the exposure amount required to obtain a density of "fog+1.0" and was shown as the relative value when the sensitivity of the control sample developed at 35° C. was defined as 100.

Also, the value of gamma was measured from a line passing through the point on the characteristic curve at a density obtained by adding 0.2 to the value of fog and the point at a density obtaied by further adding 0.8 to the aforesaid density.

In addition, the value of fog is the value including the density of the base.

As is clear from the results shown in Table 1, it can be seen that in Samples 4 to 8 using the compounds of this invention, the formation of fog is effectivelyrestrained as compared to Samples 2 and 3 using the comparison compound and in the former samples, the increase of the sensitivity in the case of processing at 37° C. only is restrained without reducing the sensitivity in the processings at 31° C. and 35° C. too much and hence these samples have less processing temperature reliance of sensitivity.

Also, in the samples of this invention, the increase of gamma in the processing at 37° C. is effectively restrained and hence the processing temperature reliance of gamma is very low. Thus, the above results show that the compounds of this invention restrain the formation of fog and the increase of sensitivity and gradation in high temperature processing and always provide stable and high quality photographic properties.

EXAMPLE 2

Each of Samples 1 to 8 as in Example 1 was exposed by the same manner as in Example 1 and subjected to the following processings using each of the following developers.

Developer A: Same as the developer used in Example 1.

Developer B: The developer was prepared by adding 11.1 g of potassium bromide per liter of Developer A. (The concentration of potassium bromide was 4 times that of Developer A.)

In addition, the fix solution has the same composition as that in Example 1.

| Processing Step | Temperature | Time |
|---|---|---|
| 1. Development | 35° C. | 25 sec |
| 2. Fix | 35° C. | 25 sec |
| 3. Wash | 20° C. | 2 min |
| 4. Drying | 55° C. | 10 min |

After processing, the photographic properties were measured and the results thus obtained are shown in Table 2.

In addition, the sensitivity in Table 2 is the reciprocal of the exposure amount required to obtain a density of fog+0.2 and was shown by the relative value when the sensitivity of Sample 1 developed at 35° C. was defined as 100.

TABLE 1

| Sample | Compound | Amount mole/mole-Ag | Fog 31° C. | Fog 35° C. | Fog 37° C. | Relative Sensitivity 31° C. | Relative Sensitivity 35° C. | Relative Sensitivity 37° C. | Sensitivity Difference (37° C.–31° C.) | Gamma 31° C. | Gamma 35° C. | Gamma 37° C. | Gamma Difference (37° C.–31° C.) |
|---|---|---|---|---|---|---|---|---|---|---|---|---|---|
| 1(Control) | — | | 0.12 | 0.15 | 0.19 | 49 | 100 | 145 | 96 | 1.55 | 2.22 | 2.63 | 1.08 |
| 2(Comparison) | Nitron* | $3.4 \times 10^{-4}$ | 0.12 | 0.14 | 0.17 | 50 | 91 | 126 | 76 | 1.60 | 2.03 | 2.45 | 0.85 |
| 3(Comparison) | " | $6.8 \times 10^{-4}$ | 0.12 | 0.14 | 0.16 | 49 | 81 | 105 | 56 | 1.60 | 1.88 | 2.08 | 0.48 |
| 4(Invention) | Compound 2 | " | 0.12 | 0.13 | 0.14 | 52 | 90 | 102 | 50 | 1.62 | 1.86 | 1.98 | 0.36 |
| 5(Invention) | Compound 17 | $3.4 \times 10^{-4}$ | 0.12 | 0.13 | 0.14 | 51 | 82 | 101 | 50 | 1.65 | 1.87 | 2.05 | 0.40 |
| 6(Invention) | Compound 23 | $1.7 \times 10^{-4}$ | 0.12 | 0.13 | 0.14 | 52 | 81 | 101 | 49 | 1.59 | 1.77 | 1.88 | 0.29 |
| 7(Invention) | Compound 7 | $3.4 \times 10^{-4}$ | 0.12 | 0.13 | 0.14 | 49 | 85 | 98 | 49 | 1.71 | 1.91 | 2.05 | 0.34 |
| 8(Invention) | Compound 22 | " | 0.12 | 0.13 | 0.14 | 51 | 84 | 101 | 50 | 1.67 | 1.87 | 2.04 | 0.37 |

*The compound described in Japanese Patent Publication No. 28,691/'77.

TABLE 2

| Sample | Compound | Amount mole/mole-Ag | Fog (A) | Fog (B) | Relative Sensitivity (A) | Relative Sensitivity (B) | Sensitivity Difference (B−A) | Gamma (A) | Gamma (B) | Gamma Difference (B)−(A) |
|---|---|---|---|---|---|---|---|---|---|---|
| 1(Control) | — | — | 0.12 | 0.15 | 100 | 132 | 32 | 2.28 | 1.90 | −0.38 |
| 2(Comparison) | Nitron | $3.4 \times 10^{-4}$ | 0.12 | 0.14 | 95 | 129 | 34 | 2.10 | 1.86 | −0.24 |
| 3(Comparison) | " | $6.8 \times 10^{-4}$ | 0.12 | 0.14 | 90 | 117 | 27 | 1.90 | 1.81 | −0.09 |

TABLE 2-continued

| Sample | Compound | Amount mole/mole-Ag | Fog (A) | Fog (B) | Relative Sensitivity (A) | Relative Sensitivity (B) | Sensitivity Difference (B−A) | Gamma (A) | Gamma (B) | Gamma Difference (B)−(A) |
|---|---|---|---|---|---|---|---|---|---|---|
| 4(Invention) | Compound 2 | " | 0.12 | 0.12 | 94 | 97 | 3 | 2.15 | 2.17 | 0.02 |
| 5(Invention) | Compound 17 | $3.4 \times 10^{-4}$ | 0.12 | 0.12 | 89 | 92 | 3 | 2.17 | 2.16 | −0.01 |
| 6(Invention) | Compound 23 | $1.7 \times 10^{-4}$ | 0.12 | 0.12 | 90 | 94 | 4 | 2.11 | 2.12 | 0.01 |
| 7(Invention) | Compound 7 | $3.4 \times 10^{-4}$ | 0.12 | 0.12 | 91 | 95 | 4 | 2.09 | 2.07 | −0.02 |
| 8(Invention) | Compound 22 | " | 0.12 | 0.12 | 89 | 90 | 1 | 2.16 | 2.14 | −0.02 |

As is clear from the results shown in Table 2, it can be seen that the Samples 4 to 8 using the compounds of this invention show very less change of photographic properties between the case of using Developer A and the case of using Developer B as compared to the Samples 2 and 3 using the comparison compound. In other words, the foregoing compounds used in this invention effectively restrain the increase of fog and sensitivity and the reduction of gamma in the development by the developer having the high concentration of potassium bromide. Usually, it is known that when a large amount of photographic materials are processed, the concentration of potassium bromide in the developer is increased but as shown in the above results, the compounds of this invention prevent the occurrence of deviation of photographic properties by the increase of the concentration of potassium bromide. This also shows that the foregoing compounds of this invention always give stable photographic properties even when a developer is fatigued.

EXAMPLE 3

By following the same procedure as in Example 1 except that each of the compounds 2 and 17 of this invention was used together with the polyoxyethylenic surface active agent [II]-2, [II]-4, [III]-2, [III]-3, [IV]-1, [IV]-3, or [IV]-6 as shown in Table 3, samples were prepared and the photographic properties were measured as in Example 1. The results thus obtained are shown in Table 3.

TABLE 3

| Sample No. | Added Compounds | Amount of the Compound mole/mole-Ag | Amount of Polyethylene Compound mg/mole-Ag | Fog 31°C. | Fog 35°C. | Fog 37°C. | Relative Sensitivity (F + 1.0) 31°C. | Relative Sensitivity (F + 1.0) 35°C. | Relative Sensitivity (F + 1.0) 37°C. | Sensitivity Difference (37°C.−31°C.) | Gamma 31°C. | Gamma 35°C. | Gamma 37°C. | Gamma Difference (37°C.−31°C.) |
|---|---|---|---|---|---|---|---|---|---|---|---|---|---|---|
| 1 | Compound 2 alone | $6.8 \times 10^{-4}$ | — | 0.12 | 0.13 | 0.14 | 52 | 90 | 102 | 50 | 1.62 | 1.86 | 1.98 | 0.36 |
| 2 | Compound 2 + POE Compound [II]-2 | " | 800 | 0.12 | 0.13 | 0.13 | 49 | 85 | 95 | 46 | 1.59 | 1.82 | 1.91 | 0.32 |
| 3 | Compound 2 + POE Compound [II]-4 | " | " | 0.12 | 0.13 | 0.14 | 51 | 84 | 95 | 44 | 1.60 | 1.81 | 1.90 | 0.30 |
| 4 | Compound 2 + POE Compound [III]-2 | " | " | 0.12 | 0.13 | 0.14 | 52 | 83 | 93 | 39 | 1.62 | 1.83 | 1.93 | 0.31 |
| 5 | Compound 2 + POE Compound [III]-3 | " | " | 0.12 | 0.13 | 0.14 | 49 | 84 | 94 | 45 | 1.61 | 1.82 | 1.92 | 0.31 |
| 6 | Compound 2 + POE Compound [IV]-1 | " | " | 0.12 | 0.13 | 0.13 | 51 | 82 | 92 | 41 | 1.60 | 1.80 | 1.90 | 0.30 |
| 7 | Compound 2 + POE Compound [IV]-3 | " | " | 0.12 | 0.13 | 0.14 | 51 | 84 | 93 | 42 | 1.59 | 1.81 | 1.91 | 0.32 |
| 8 | Compound 2 + POE Compound [IV]-6 | " | " | 0.12 | 0.13 | 0.14 | 50 | 85 | 95 | 45 | 1.62 | 1.82 | 1.92 | 0.30 |
| 9 | Compound 17 alone | $3.4 \times 10^{-4}$ | 800 | 0.12 | 0.13 | 0.14 | 51 | 82 | 101 | 50 | 1.65 | 1.87 | 2.05 | 0.30 |
| 10 | Compound 17 + POE Compound [II]-2 | " | " | 0.12 | 0.13 | 0.13 | 49 | 78 | 94 | 45 | 1.62 | 1.83 | 1.97 | 0.35 |
| 11 | Compound 17 + POE Compound [III]-2 | " | " | 0.12 | 0.13 | 0.14 | 52 | 77 | 92 | 40 | 1.59 | 1.80 | 1.92 | 0.33 |
| 12 | Compound 17 + POE Compound [IV]-1 | " | " | 0.12 | 0.13 | 0.13 | 50 | 75 | 91 | 41 | 1.63 | 1.82 | 1.96 | 0.33 |
| 13 | Compound 17 + POE Compound [IV]-3 | " | " | 0.12 | 0.13 | 0.14 | 50 | 78 | 92 | 42 | 1.62 | 1.82 | 1.97 | 0.35 |

As is clear from the results in Table 3, it is seen that when the compound of this invention shown by formula (I) is used together with the polyoxyethylenic surface active agent shown by formula (II), (III) or (IV), the extent of the deviation of the photographic characters by the change of the processing condition is greatly reduced. That is, it is seen that the use of both the foregoing compounds further restrain the extents of increasing the fog, sensitivity, and gamma with the increase of the processing temperature.

While the invention has been described in detail and with reference to specific embodiments thereof, it will be apparent to one skilled in the art that various changes and modifications can be made therein without departing from the spirit and scope thereof.

What is claimed is:

1. A silver halide photographic material which is developed by a processing liquid comprising a support having thereon at least one silver halide emulsion layer, wherein said silver halide photographic material contains in at least one hydrophilic layer thereof a compound selected from the group consisting of compounds represented by formula (I) and salts formed from said compound and an acid;

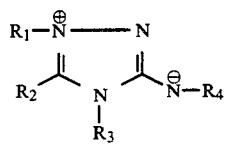

(I)

wherein $R_1$, $R_2$, $R_3$ and $R_4$ each represents a substituted or unsubstituted alkyl group, a substituted or unsubstituted alkenyl group, a substituted or unsubstituted cycloalkyl group, a substituted or unsubstituted aryl group, or a substituted or unsubstituted heterocyclic ring group; or one or both of said $R_1$ and $R_2$ and said $R_3$ and $R_4$ combine with each other to form a ring wherein the compound represented by formula (I) is present in an amount effective to prevent the formation of fog occurring upon high temperature quick processing, control the development speed, and provide a high-quality image.

2. A silver halide photographic material as in claim 1, wherein said substituted or unsubstituted alkyl group has from 1 to 30 carbon atoms.

3. A silver halide photographic material as in claim 1, wherein said substituted or unsubstituted alkenyl group has from 3 to 30 carbon atoms.

4. A silver halide photographic material as in claim 1, wherein said substituted or unsubstituted cycloalkyl group has from 3 to 30 carbon atom.

5. A silver halide photographic material as in claim 1, wherein said substituted or unsubstituted aryl group has from 6 to 30 carbon atoms.

6. A silver halide photographic material as in claim 1, wherein said substituted or unsubstituted heterocyclic ring group has from 1 to 30 carbon atoms.

7. A silver halide photographic material as in claim 1, wherein said substituted groups each has at least one substituent selected from the group consisting of a halogen atom, an alkoxy group, an aryloxy group, an amino group, an alkyl amino group, an aryl amino group, a hydroxy group, a cyano group, a nitro group, an acyl amino group, a carbamoyl group, an acyl group, a sulfonyl group, a sulfamoyl group, a sulfonamide group, an acyloxy group, an alkoxycarbonyl group, a carboxyl group and a sulfonic acid group.

8. A silver halide photographic material as in claim 1, wherein said ring group formed by combining $R_1$ and $R_2$, or $R_3$ and $R_4$ is a 5 or 6 membered hydrocarbon ring group.

9. A silver halide photographic material as in claim 1, wherein said acid is selected from the group consisting of acetic acid, nitric acid, salicylic acid, hydrochloric acid, hydriodic acid and hydrobromic acid.

10. A silver halide photographic material as in claim 1, wherein said hydrophilic colloid layer is selected from the group consisting of a silver halide emulsion layer, a subbing layer, a protective layer, an interlayer, a filter layer, and an antihalation layer.

11. A silver halide photographic material as in claim 1, wherein said compound is contained in an amount of from $10^{-8}$ to $10^{-1}$ mole per mole of silver in the silver halide photographic material.

12. A silver halide photographic material as in claim 1, wherein said hydrophilic colloid layer is a silver halide emulsion layer.

13. A silver halide photographic material as in claim 1, wherein said silver halide photographic material further contains a polyalkylene oxide.

14. A silver halide photographic material as in claim 13, wherein said polyalkylene oxide is represented by formula (II):

$$R-A-CH_2CH_2O)_{n_1}H \qquad (II)$$

wherein R represents a substituted or unsubstituted alkyl group having 1 to 30 carbon atoms, alkenyl group having 3 to 30 carbon atoms or aryl group having 6 to 30 carbon atoms; A represents —O— group, —S— group, —COO— group,

(wherein $R_{11}$ represents a hydrogen atom or a substituted or unsubstituted alkyl group); and $n_1$ represents a number of 2 to 50.

15. A silver halide photographic material as in claim 13, wherein said polyalkylene oxide is represented by formula (III):

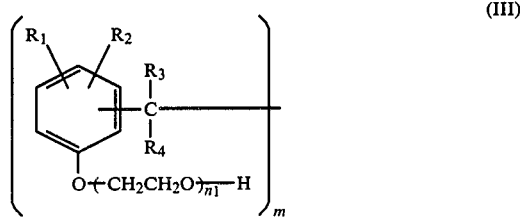

(III)

wherein $R_1$ and $R_2$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; $R_3$ and $R_4$ each represents a hydrogen atom, a substituted or unsubstituted alkyl group, aryl group or α-furyl group, or said $R_3$ and $R_4$ combine with each other to form a ring; and $n_1$ and m each represents a number of 2 to 50.

16. A silver halide photographic material as in claim 13, wherein said polyalkylene oxide is represented by formula (IV):

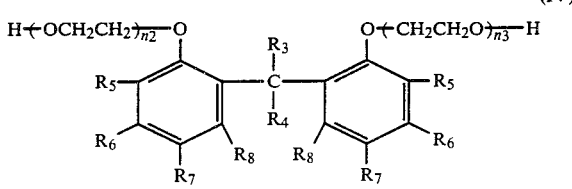

wherein $R_3$ and $R_4$ each represents a hydrogen atom, a substituted or unsubstituted alkyl group, aryl group or α-furyl group or said $R_3$ and $R_4$ combine with each other to form a ring; $R_5$ and $R_7$ each represents a substituted or unsubstituted alkyl group, aryl group, or alkoxy group, a halogen atom, an acyl group, an amido group, a sulfonamido group, a carbamoyl group or a sulfamoyl group; $R_6$ and $R_8$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; or one or more of said $R_5$ and $R_6$, said $R_6$ and $R_7$ and said $R_7$ and $R_8$ combine with each other to form a substituted or unsubstituted ring; and $n_2$ and $n_3$ each represents a number of 2 to 50.

17. A silver halide photographic material as in claim 13, wherein said polyalkylene oxide is contained in an amount of from 5 to 500 mg/m².

18. A silver halide photographic material as in claim 15, wherein the weight ratio of the amount of at least one of compounds represented by formula (I) and salts thereof to the amount of said polyalkylene oxide is from 1/10 to 100.

19. A silver halide photographic material as in claim 11, wherein said compound is contained in an amount of not more than $1 \times 10^{-2}$ mole per mole of silver in the photographic material.

20. A method for obtaining a silver image from a silver halide photographic material comprising a support having thereon at least one silver halide emulsion layer, which comprises (i) incorporating in at least one hydrophilic layer of said silver halide photographic material at least one compound selected from the group consisting of compounds represented by formula (I) and salts formed from said compound and an acid;

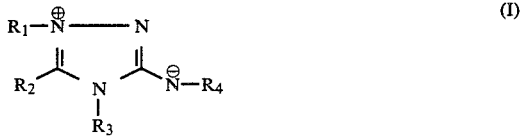

wherein $R_1$, $R_2$, $R_3$ and $R_4$ each represents a substituted or unsubstituted alkyl group, a substituted of unsubstituted alkenyl group, a substituted or unsubstituted cycloalkyl group, a substituted or unsubstituted aryl group, or a substituted or unsubstituted heterocyclic ring group; or one or both of said $R_1$ and $R_2$ and said $R_3$ and $R_4$ combine with each other to form a ring, (ii) exposing to light, and (iii) developing the material exposed with a processing liquid and wherein the compound represented by formula (I) is present in an amount effective to prevent the formation of fog occurring upon high temperature quick processing, control the development speed, and provide a high-quality image.

21. A method for obtaining a silver image as in claim 20, wherein development is conducted at a temperature of from 18° C. to 50° C.

22. A method for obtaining a silver image as in claim 20, wherein development is conducted at a temperature of from 30° C. to 50° C.

23. A method for obtaining a silver image as in claim 22, wherein the processing time of development is from 20 to 240 seconds.

24. A method for obtaining a silver image as in claim 22, wherein said development is for a black and white photographic process and the processing time of development is from 20-150 seconds.

25. A method for obtaining a silver image as in claim 22, wherein said development is for a color photographic process and the processing time of development is from 120 to 240 seconds.

26. A method for obtaining a silver image as in claim 20, wherein said compound is contained in an amount of from $10^{-8}$ to $10^{-1}$ mole per mole of silver in the silver halide photographic material.

27. A method for obtaining a silver image as in claim 20, wherein said silver halide photographic material further contains a polyalkylene oxide.

28. A method for obtaining a silver image as in claim 20, wherein said polyalkylene oxide is represented by formula (II):

$$R\text{—}A\text{—}(CH_2CH_2O)_{n_1}H \qquad (II)$$

wherein R represents a substituted or unsubstituted alkyl group having 1 to 30 carbon atoms, alkenyl group having 3 to 30 carbon atoms or aryl group having 6 to 30 carbon atoms; A represents —O— group, —S— group, —COO— group,

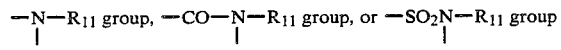

(wherein $R_{11}$ represents a hydrogen atom or a substituted or unsubstituted alkyl group); and $n_1$ represents a number of 2 to 50.

29. A method for obtaining a silver image as in claim 20, wherein said polyalkylene oxide is presented by formula (III):

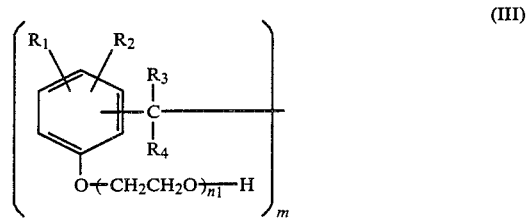

wherein $R_1$ and $R_2$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; $R_3$ and $R_4$ each represents a hydrogen atom, a substituted or unsubstituted alkyl group, aryl group or α-furyl group, or said $R_3$ and $R_4$ combine with each other to form a ring; and $n_1$ an m each represents a number of 2 to 50.

30. A method for obtaining a silver image as in claim 20, wherein said polyalkylene oxide is represented by formula (IV):

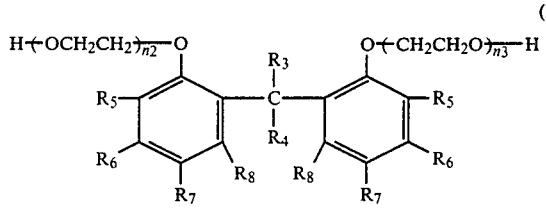

(IV)

wherein $R_3$ and $R_4$ each represents a hydrogen atom, a substituted or unsubstituted alkyl group, aryl group or α-furyl group or said $R_3$ and $R_4$ combine with each other to form a ring; $R_5$ and $R_7$ each represents a substituted or unsubstituted alkyl group, aryl group, or alkoxy group, a halogen atom, an acyl group, an amido group, a sulfonamido group, a carbamoyl group or a sulfamoyl group; $R_6$ and $R_8$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; or one or more of said $R_5$ and $R_6$, said $R_6$ and $R_7$ and said $R_7$ and $R_8$ combine with each other to form a substituted or unsubstituted ring; and $n_2$ and $n_3$ each represents a number of 2 to 50.

31. A method for obtaining a silver image as in claim 20, wherein said polyalkylene oxide is contained in an amount of from 5 to 500 mg/m².

32. A method for obtaining a silver image as in claim 20, wherein the weight ratio of the amount of at least one of compounds represented by formula (I) and salts thereof to the amount of said polyalkylene oxide is from 1/10 to 100.

33. A method for obtaining a silver image as in claim 20, wherein said compound is contained in an amount of not more than $1 \times 10^{31\ 2}$ mole per mole of silver in the photographic material.

34. A method for obtaining a silver image as in claim 20, wherein the polyalkyleneoxide is one member selected from the group consisting of the polyalkylenoxide represented by the formula (II):

$$R-A-CH_2CH_2O)_{n_1}H \qquad (II)$$

wherein R represents a substituted or unsubstituted alkyl group having 1 to 30 carbon atoms, alkenyl group having 3 to 30 carbon atoms or aryl group having 6 to 30 carbon atoms; A represents —O— group, —S— group, —COO— group,

(wherein $R_{11}$ represents a hydrogen atom or a substituted or unsubstituted alkyl group); and $n_1$ represents a number of 2 to 50;

the polyalkyleneoxide represented by the formula (III):

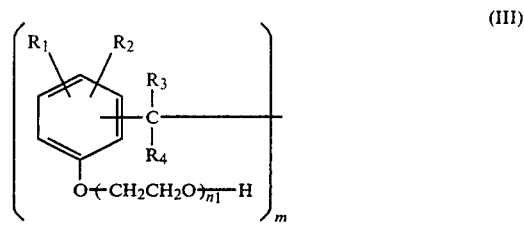

(III)

wherein $R_1$ and $R_2$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; $R_3$ and $R_4$ each represents a hydrogen atom, a substituted or unsubstituted alkyl group, aryl group or α-furyl group, or said $R_3$ and $R_4$ combine with each other to form a ring; and $n_1$ an m each represents a number of 2 to 50;

and the polyalkyleneoxide represented by the formula (IV):

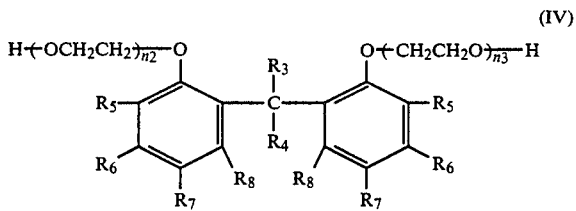

(IV)

wherein $R_3$ and $R_4$ each represents a hydrogen atom, a substituted or unsubstituted alkyl group, aryl group a α-furyl group or said $R_3$ and $R_4$ combine with each other to form a ring; $R_5$ and $R_7$ each represents a substituted or unsubstituted alkyl group, aryl group, or alkoxy group, a halogen atom, an acyl group, an amido group, a sulfonamido group, a carbamoyl group or a sulfamoyl group; $R_6$ and $R_8$ each represents a hydrogen atom, a substituted or unsubstituted alkyl group, aryl group, or alkoxy group, a halogen atom, an acyl group, an amido group, a sulfonamido group, a carbamoyl group, or a sulfamoyl group; or one or more of said $R_5$ and $R_6$, said $R_6$ and $R_7$ and said $R_7$ and $R_8$ combine with each other to form a substituted or unsubstituted ring; and $n_2$ and $n_3$ each represents a number of 2 to 50.

* * * * *